(12) United States Patent
Childs et al.

(10) Patent No.: US 10,940,065 B2
(45) Date of Patent: Mar. 9, 2021

(54) ANGLE CALIBRATION USING LOAD CELLS

(71) Applicant: Stryker Corporation, Kalamazoo, MI (US)

(72) Inventors: William Childs, Kalamazoo, MI (US); Gary Bartley, Kalamazoo, MI (US); Connor St. John, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 16/549,612

(22) Filed: Aug. 23, 2019

(65) Prior Publication Data
US 2020/0060907 A1 Feb. 27, 2020

Related U.S. Application Data

(60) Provisional application No. 62/722,368, filed on Aug. 24, 2018.

(51) Int. Cl.
*A61G 7/005* (2006.01)
*G01P 15/18* (2013.01)
(Continued)

(52) U.S. Cl.
CPC ............. *A61G 7/005* (2013.01); *A61G 7/008* (2013.01); *G01G 19/52* (2013.01); *G01P 15/18* (2013.01); *A61G 7/018* (2013.01)

(58) Field of Classification Search
CPC .. A61G 7/0506; A61G 7/0514; A61G 7/0524; A61G 7/008; A61G 7/0527;
(Continued)

(56) References Cited

U.S. PATENT DOCUMENTS 4,869,266 A 9/1989 Taylor et al.
7,702,481 B2 4/2010 Dionne et al.
(Continued)

OTHER PUBLICATIONS

Experimental investigations of the roll load and roll torquewhen high strength steel is roll formed, journal of Materials Processing Technology 191 (2007) 44-47, Michael Lindgren. (Year: 2007).*
(Continued)

*Primary Examiner* — Jacques M Saint Surin
(74) *Attorney, Agent, or Firm* — Christopher G. Darrow; Darrow Mustafa PC

(57) ABSTRACT

An automated system and methods are provided for calibrating an accelerometer of a patient support apparatus using a load cell. The patient support apparatus includes a litter frame and a deck supported by the litter frame, movable between various angled positions. A patient support surface is arranged on the deck and configured to support a patient thereon. The patient support surface has at least one region configured to be disposed at an angular position. A load cell is provided, configured to generate load data including first and second load outputs detected at first and second trend angles with respect to a horizontal plane. An accelerometer is provided, configured to generate angle data including first and second angle outputs representative of the trend angles. A controller in communication with the load cell and the accelerometer determines an error in the angle data and calibrates the accelerometer.

20 Claims, 11 Drawing Sheets

(51) Int. Cl.
  *G01G 19/52* (2006.01)
  *A61G 7/008* (2006.01)
  *A61G 7/018* (2006.01)

(58) Field of Classification Search
  CPC ...... A61G 7/0528; A61G 7/005; A61G 7/015;
  A61G 2203/42; A61G 2203/32; A61G
  7/018; A61G 2203/34; G01G 19/445;
  G01G 19/52; G01P 15/18; G01P 21/00;
  A61B 5/1115; A61B 5/1121; A61B
  5/6892
  USPC .......................................................... 177/144
  See application file for complete search history.

(56) References Cited

U.S. PATENT DOCUMENTS

| | | |
|---|---|---|
| 10,330,522 B2 | 6/2019 | Paul et al. |
| 2006/0259267 A1 | 11/2006 | Narayanasamy |
| 2011/0083271 A1 | 4/2011 | Bhai |
| 2014/0237721 A1 | 8/2014 | Lemire et al. |
| 2016/0110445 A1* | 4/2016 | Andrews ............... G06F 16/338 707/748 |
| 2017/0003159 A1* | 1/2017 | Kostic .................. G01G 19/445 |
| 2017/0234723 A1* | 8/2017 | Charles ................ A61B 5/1036 5/600 |
| 2018/0110445 A1* | 4/2018 | Bhimavarapu ...... A61B 5/0017 |

OTHER PUBLICATIONS

IEEE Transactions on Industry Applications, vol. 29, No. 4, Jul./Aug. 1993 727, Tension Control: Dancer or lOAD Cells, Rolls Norbert A. Ebler, Ragnar Arnason, Gerd Michaelis, (Year: 1993).*

* cited by examiner

| X Axis Orientation to Horizon (°) | X Output | | Y Output (g) | |
|---|---|---|---|---|
| | X Output (g) | Δ per Degree of Tilt (mg) | Y Output (g) | Δ per Degree of Tilt (mg) |
| −90 | −1.000 | −0.2 | 0.000 | 17.5 |
| −75 | −0.966 | 4.4 | 0.259 | 16.9 |
| −60 | −0.866 | 8.6 | 0.500 | 15.2 |
| −45 | −0.707 | 12.2 | 0.707 | 12.4 |
| −30 | −0.500 | 15.0 | 0.866 | 8.9 |
| −15 | −0.259 | 16.8 | 0.966 | 4.7 |
| 0 | 0.000 | 17.5 | 1.000 | 0.2 |
| 15 | 0.259 | 16.9 | 0.966 | −4.4 |
| 30 | 0.500 | 15.2 | 0.866 | −8.6 |
| 45 | 0.707 | 12.4 | 0.707 | −12.2 |
| 60 | 0.866 | 8.9 | 0.500 | −15.0 |
| 75 | 0.966 | 4.7 | 0.259 | −16.8 |
| 90 | 1.000 | 0.2 | 0.000 | −17.5 |

US 10,940,065 B2

ANGLE CALIBRATION USING LOAD CELLS

CROSS-REFERENCE TO RELATED APPLICATION

This application claims priority to U.S. Provisional Patent Application Ser. No. 62/722,368, filed on Aug. 24, 2018, and which is incorporated by reference in its entirety.

BACKGROUND

In the day to day operations of medical facilities, patients may need to be weighed. In many instances, patients are not ambulatory and using a free-standing scale may not otherwise be feasible.

Patient support systems facilitate care of patients in a health care setting. Exemplary patient support systems include patient support apparatuses such as hospital beds, stretchers, gurneys, cots, trolleys, and wheelchairs, as well as traditional chairs, seats, benches, and tables. The patient support apparatuses have the potential of being in numerous different positioning orientations as the litters and support components attached thereto typically have several sections, such as a fowler section, a seat section, and a foot section, with the fowler and foot sections being capable of articulation relative to the seat section. Patient support apparatuses often have one or more load sensors that may be configured to measure a weight of various areas of the apparatus, including a weight of the patient. One difficulty with determining the patient's weight occurs when the patient support apparatus is articulated or at positions other than a horizontally flat base position, at which load cells are usually calibrated. For example, when the patient support apparatus is articulated at various angles, the raw measurements from typical load cells will not reflect a patient's accurate weight because the center of gravity of the load shifts, affecting the individual load signals sensed by each load cell. Caregivers and medical personnel require accurate readings a patient's weight independent of the articulation.

Accelerometers, or tilt sensors that incorporate an accelerometer, can be used to provide an effective way to measure the inclination in the patient's position. Thus, the load cell measurements can be used together with the articulation angle of a section in order to accurately determine the patient's weight. Accelerometers are typically calibrated at the time of manufacturing the patient support apparatus, for example, using an inclinometer. However, over time or as the result of various events or location of use, the accelerometers can experience drift and/or other variations within sensor parameters. The variations can cause, for example, reduced accuracy of data, leading to incorrect patient weights.

The process of recalibrating an accelerometer with an inclinometer when outside of the manufacturing facility can be error prone or complex. For example, the calibration processes may require particular preconfigured environments or environments with particular characteristics in order to achieve a proper calibration. Accordingly, alternate methods for recalibrating accelerometers are desired.

BRIEF DESCRIPTION OF THE DRAWINGS

The present teachings will become more fully understood from the detailed description and the accompanying drawings, wherein.

It should be noted that the figures set forth herein are intended to exemplify the general characteristics of the systems, methods, and devices among those of the present technology, for the purpose of the description of certain aspects. These figures may not precisely reflect the characteristics of any given aspect, and are not necessarily intended to define or limit specific embodiments within the scope of this technology. Further, certain aspects may incorporate features from a combination of figures, while other aspects may incorporate only portions of features from a single figure.

DETAILED DESCRIPTION

The present technology generally provides automated systems and methods for calibrating an accelerometer. The calibration accuracy of an accelerometer is fundamentally dependent on, and proportional to, the force of gravity at the site of operation. The absolute sensitivity may differ from the location of the place of manufacture. This is because the acceleration due to gravity varies across the Earth's surface, which may translate to a variation of up to about 0.5%, depending on the differences between the original calibration location and the measurement location. Scales that use load cells as weight sensors effectively measure the force of gravity acting upon a mass. If the on-site gravity compensation is not taken into account, the scale reading may have an error that is proportional to the difference between the acceleration due to gravity between the location of use and the original calibration site. Additionally, either over time or as the result of various events, the accelerometers can experience drift and/or other variations within sensor parameters.

In various aspects, the accelerometers calibrated according to the present technology are part of a patient support apparatus that uses load cells to obtain weight measurements. In particular, the systems and methods provide an angle calibration using an output of at least one load cell at two different trend angles. With the two outputs at known angles, and using a known weight, an algorithm can be used to determine an error in the accelerometer, and to calibrate the accelerometer. It is envisioned that the calibration can be performed locally, and does not require particular preconfigured environments or environments with particular characteristics in order to achieve a proper calibration.

Figure 1:
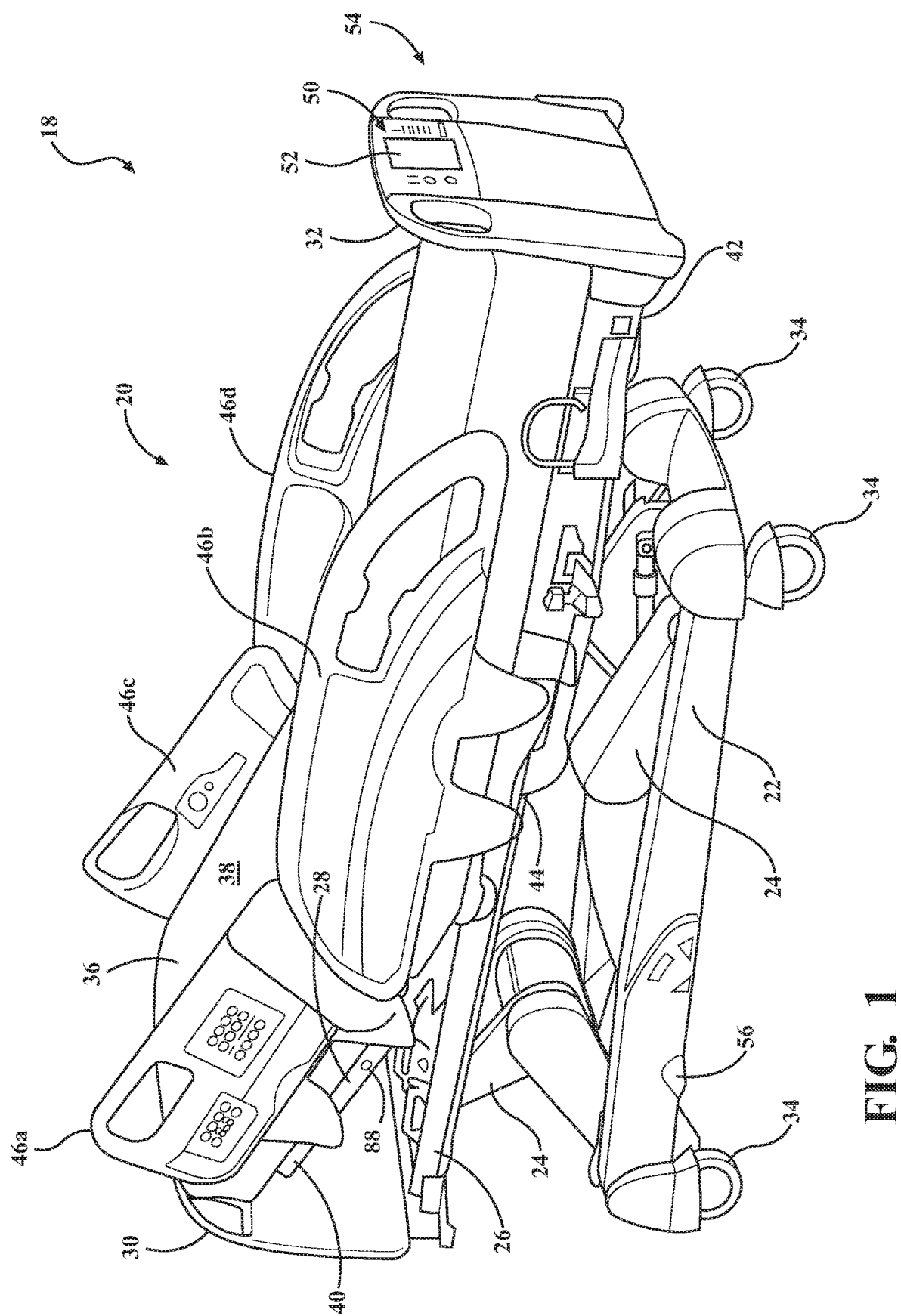
FIG. 1 is side perspective view of a patient support apparatus provided as a gatch-type hospital bed with the head section in an elevated position.
Figure 2:
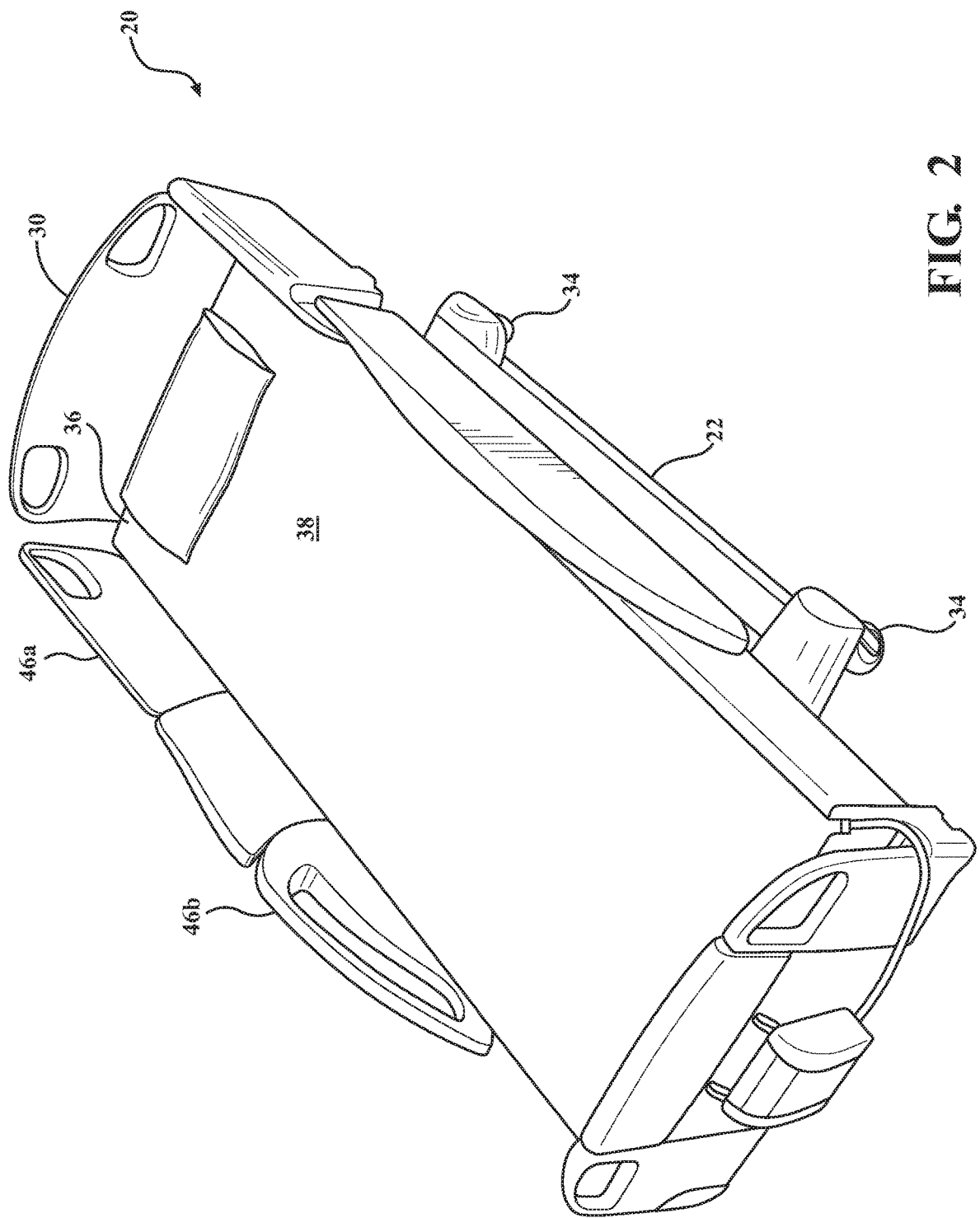
FIG. 2 is a side perspective view of a patient support apparatus provided as a gatch-type hospital bed in a substantially horizontal position.

For a more complete understanding of the present teachings, initial reference is made to FIGS. 1-2, illustrating examples of a patient support apparatus 18 with an adjustable frame that is configured as a bed 20 and generally adapted for use in a hospital or other medical setting. FIG. 1 is a side perspective view of a first exemplary bed 20 with a raised head section; FIG. 2 is a side perspective view of a second exemplary bed in a horizontal position. Although the particular form of patient support apparatus illustrated in FIGS. 1-2 is a bed, it should be understood that patient support apparatuses useful with the present technology may include, in different embodiments, stretchers; gurneys; cots; trolleys; operating tables; benches; wheelchairs, as well as traditional chairs, seats, and recliners; or any other similar type of structure capable of supporting a patient and having the hardware and software for obtaining a weight measurement of the patient, whether stationary or mobile and/or whether used for medical or residential environments. In still other aspects, the patient support apparatus may be configured to change in shape and function, for example, between a stretcher or bed and a chair.

The exemplary gatch-type hospital bed 20 as shown in FIGS. 1-2 includes a base 22, an automated drive system such as a pair of lifts 24, an adjustable frame commonly referred to as a litter frame assembly 26, a patient support deck 28, a headboard 30, and a footboard 32. The base 22 includes a plurality of wheels 34 that can be selectively locked and unlocked so that, when unlocked, the patient support apparatus 18 is able to be wheeled to different locations. Certain of the wheels 34 may be steering type wheels, with castors or otherwise configured to rotate up to 360 degrees, other wheels may not be rotatable. The base 22 may include one or more retractable wheels (not shown) to provide controlled traction and cornering. The base 22 may also include on or more powered wheels, the movement of which can be operated by a controller. Certain wheels 34 may be provided with locking mechanisms (not specifically shown). The lifts 24 are generally configured to raise and lower the litter frame 26 with respect to the base 22. In this regard, the lifts 24 may include hydraulic actuators, electric actuators, or any other suitable device for raising and lowering the litter frame 26 with respect to the base 22. In some embodiments, the lifts 24 may operate independently so that the orientation of litter frame 26 with respect to the base 22 may also be adjusted. The lifts 24 may be of various designs; certain lifts 24 are configured to raise and lower extending legs or columns in a substantially vertical direction, while others include hinges or scissor type lift mechanisms having linked, folding supports in a crisscross or 'X' pattern.

The litter frame 26 of the bed 20 provides a structure for coupling with the support deck 28, a headboard 30, and a footboard 32. The supporting deck 28 provides a surface on which a mattress 36, or other support member, is positioned or arranged defining a patient support surface 38 where a patient may lie and/or sit thereon. The support deck 28 may be made of a plurality of sections, some of which are pivotable about generally horizontal pivot axes. In the embodiment shown in FIG. 1, the support deck 28 includes a head section 40, a foot section 42, and one or more intermediate sections 44. The head section 40, which is also sometimes referred to as a fowler section, is pivotable with respect to the intermediate section 44 between a generally horizontal orientation (shown in FIG. 2) and a plurality of raised positions (one of which is shown in FIG. 1). The foot section 42, which is also sometimes referred to as a gatch section, is also pivotable with respect to the intermediate section 44 between a generally horizontal orientation (shown in FIGS. 1-2) and a plurality of lowered positions (not shown). In certain aspects, the head section 40 may be lowered, and the foot section 42 may be raised or elevated, with respect to the intermediate section 44, for example to increase blood flow to the upper body. The base 22, the lifts 24, the litter frame 26, the support deck 28 and its various sections 40, 42, 44, as well as other movable components, may each be provided with the necessary mechanical structures, actuators, automated drive mechanisms, etc. for exhibiting independent and automated movement, control, and related capabilities in order to provide various preferential transfer configurations of the patient support apparatuses 18.

The various patient support apparatuses 18 may also include a plurality of side rails, collectively referred to by reference number 46. For example, the bed of FIG. 1 includes a right head side rail 46a, a right foot side rail 46b, a left head side rail 46c, and a left foot side rail 46d. The side rails 46 are generally movable between a raised position and a lowered position, and in various aspects can be locked or provided at intermediate positions. The side rails 46 can be provided with handle areas for use by the patient or caregiver. In the configuration shown in FIGS. 1-2, all four of the side rails 46 are raised. As shown in FIG. 1, the interior side of the head side rails 46a, 46c may be provided with a patient control interface 48 configured to operate movement of the head section 40 and foot section 42, as well as control other auxiliary features, such as lights, televisions, sound control, and the like. The exterior side of the head side rails 46a, 46c may be provided with a caregiver control interface 50, similarly configured to operate movement of the bed 20, as well as other functions.

As shown in FIG. 1, the footboard 32 may also be provided with one or more caregiver control interface 50 and/or display 52 with optional touchscreen capabilities. In certain aspects, the footboard 32 may include a controller 54 that includes the caregiver control interface 50 and display 52. The controller 54 may include at least one processor with memory and software programmable to control various aspects of the bed 20. The teachings of the present technology may be used with known control systems and may generally include a computing device or controller 54, such as a control module with a processor, a memory, and an interface 50. It should be understood that although particular systems or subsystems may be separately defined herein, each or any of the systems may be otherwise modified, combined, or segregated via appropriate hardware and/or software as is known to those of ordinary skill in the art. The controller 54 may be a portion of another control device, a stand-alone unit, or other system, including cloud based. Alternatively, the controller 54 can be composed of multiple computing devices. The processor(s) may be any type of conventional microprocessor having desired performance characteristics and capable of manipulating or processing data and other information. The memory may include any type of computer readable medium that stores data and control algorithms described in more detail below. Other operational software for the processor may also be stored in the memory. The interface may facilitate communication with other systems, sensors, and other on-board systems. On-board systems and sensors may include, but are not limited to, weight sensors, diagnostic sensors, auxiliary systems and accessories, automated controls, and the like. The controller 54 can also include secondary, additional, or external storage, for example, a memory card, flash drive, or any other form of computer readable medium. Installed applications can be stored in whole or in part in the external storage and loaded into the memory as needed for processing.

In various aspects, the controller 54 may be located out of view, for example, secured in the base 22 or coupled to the litter frame 26, as appropriate. The controller 54 may alternatively be an external unit that is wired to the bed 20 or communicates via wireless communication. Thus, the bed 20 may also be provided with one or more communication module configured to establish a wireless communication. Various wireless communication protocols may be used, including Bluetooth, near-field communication (NFC), infrared communication, radio wave communication, cellular network communication, and wireless local area network communication (Wi-Fi). In certain aspects, the communication module may be a part of the controller 54. The wireless communication may provide compatibility with information management systems. Not only can the patient support apparatuses 18 be coupled to the controller 54 using wireless communication protocols, one or more patient support apparatuses 18 can establish a communication link directly or indirectly with one another in order to share data, information, and exhibit control.

Figure 3:
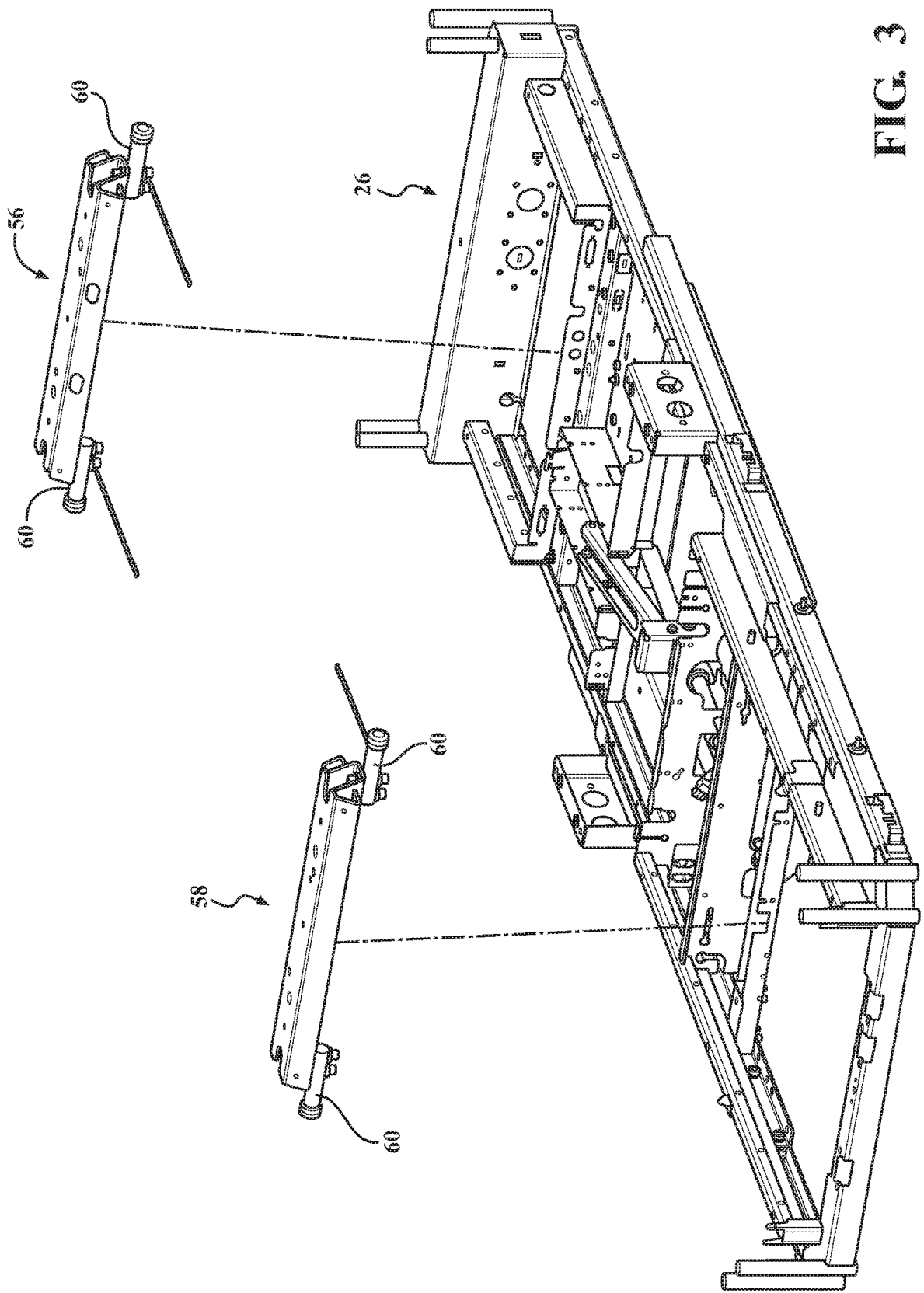
FIG. 3 is a perspective view of a litter frame useful with the patient support apparatus of FIG. 1 or 2, shown with a pair of lift header assemblies having respective pairs of load cells according to the present technology.
Figure 4:
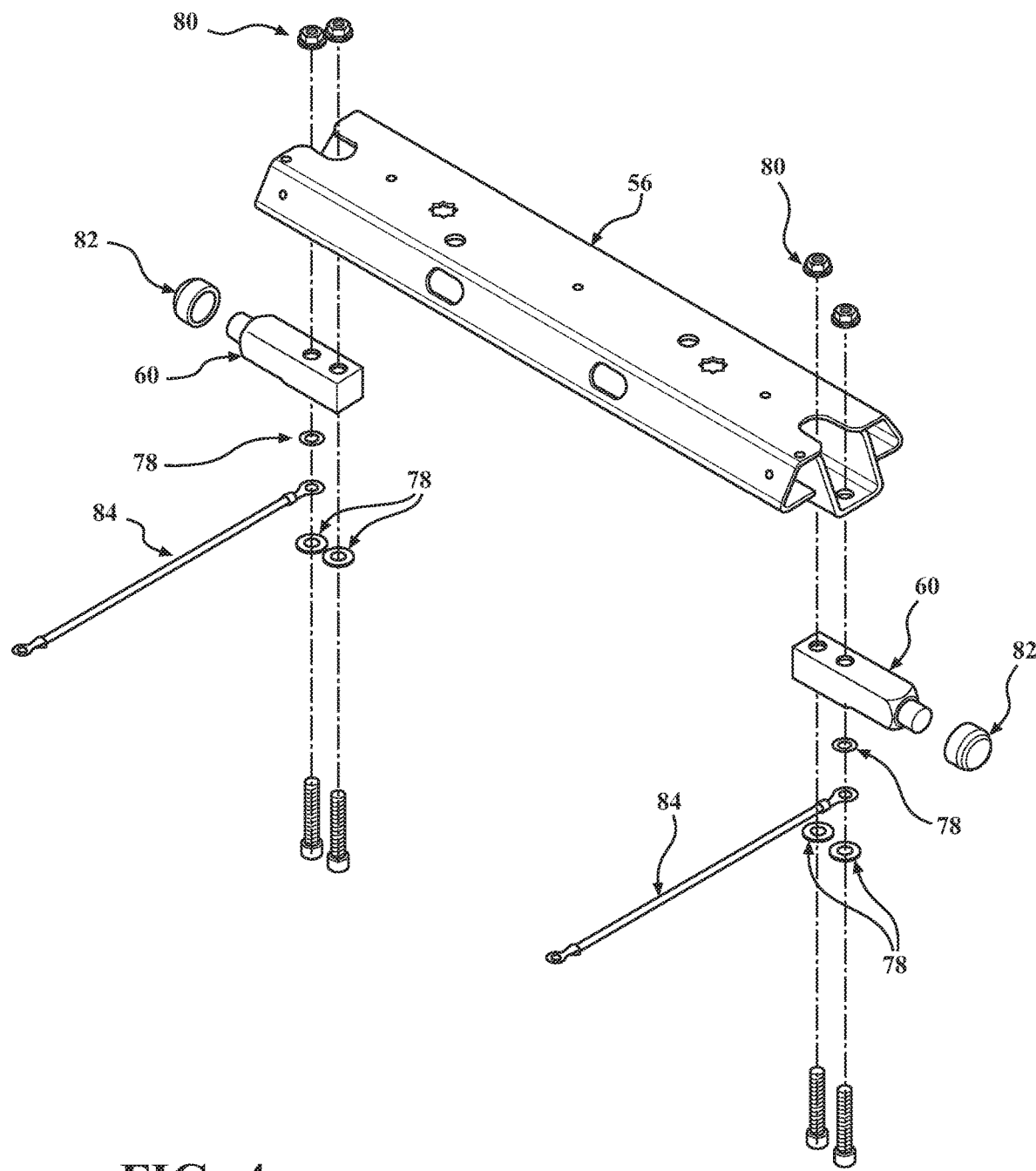
FIG. 4 is an exploded perspective view of one of the lift header assemblies as shown in FIG. 3.

FIG. 3 is a perspective view of an exemplary litter frame 26 useful with the patient support apparatus 20 of FIG. 1 or 2, shown with a pair of front and rear lift header assemblies 56, 58. While each lift header assembly 56, 58 is provided having a respective pair of load cells 60, it should be understood that different numbers of load cells may be used in accordance with the principles of the present technology. For simplicity, the litter frame 26 of FIG. 3 is shown separated from the base 22 and the lifts 24, and without the support deck 28. In an assembled state, the litter frame 26 is supported by the two lift header assemblies 56, 58, which are shown elevated from the litter frame 26 for clarity. FIG. 4 is an exploded perspective view of the front header assembly 56 as shown in FIG. 3. When assembled, the front lift header assembly 56 is coupled to a top of a first one of the lifts 24, the rear lift header assembly is coupled to a top of a second one of the lifts 24. The load cells 60 are configured to support the litter frame 26. In the non-limiting aspect shown in the figures, the load cells 60 are configured such that they provide complete and exclusive mechanical support for the litter frame 26 and all of the other components that are supported on the litter frame 26, for example, the support deck 28, the headboard 30, the footboard, 32, side rails 46, etc. With this design, the load cells 60 are configured to detect the weight of not only those components of the patient support apparatus 20 that are supported by the litter frame 26 (including the litter frame 26 itself), but also any objects or persons that are wholly or partially being supported by the support deck 28.

Figure 5:
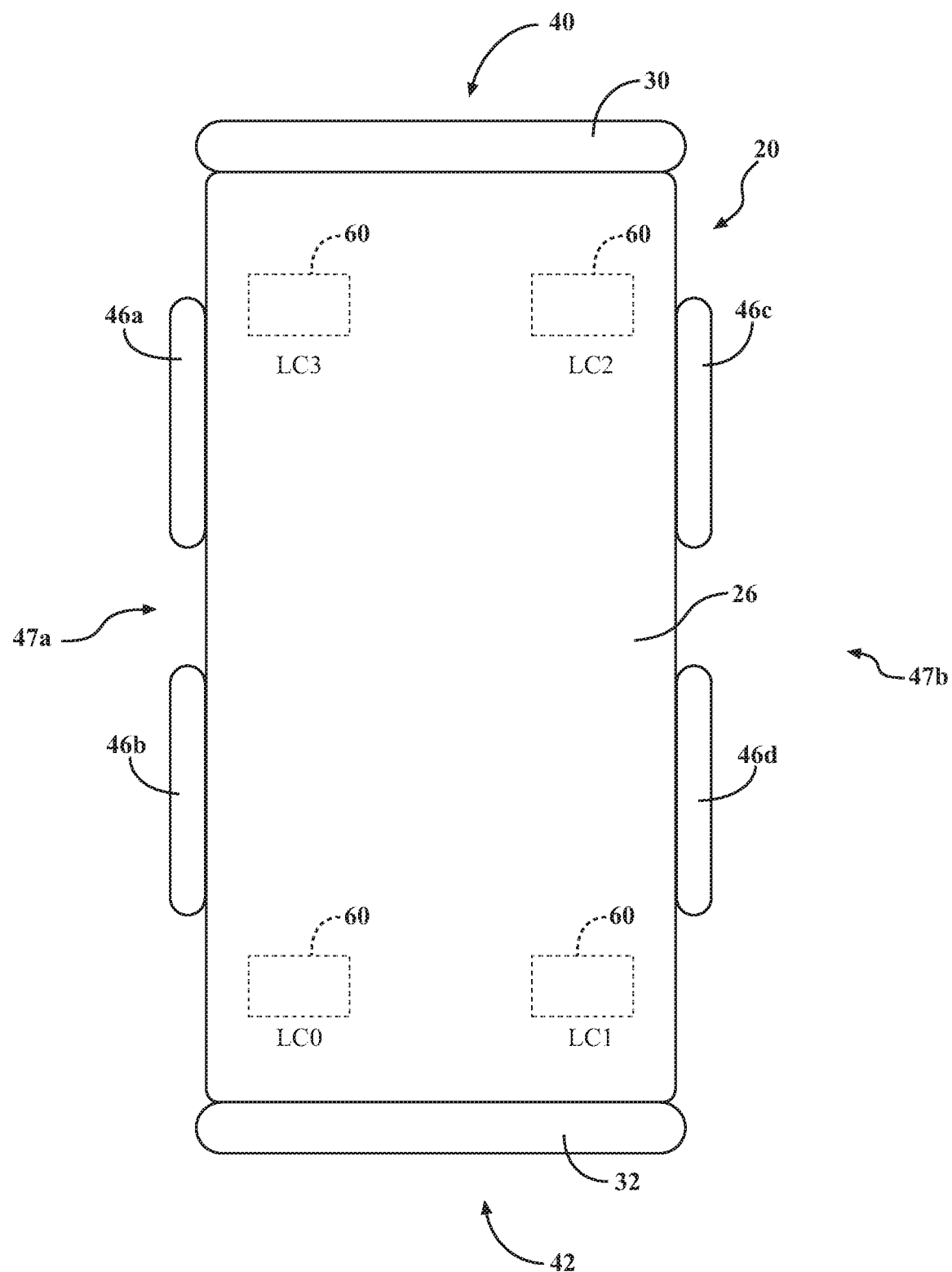
FIG. 5 shows a plan view diagram of an illustrative layout of the load cells.

FIG. 5 shows a plan view diagram of an illustrative layout of the load cells 60. Load cells 60 can be positioned at one or more locations in the frame system of the bed 20 such that measurements of various load signals can be achieved. The load cells 60 generate load signals indicative of forces applied to the load cells 60. FIGS. 3 and 5 illustrate one aspect of the present technology where the load cells 60 are respectively located proximate to the four corners of the litter frame 26, with the litter frame 26 being operatively connected to the lifts 24 and base 22 via the system of load cells 60. As shown, a first load cell labeled LC0 is positioned adjacent a foot section 42 of the patient support apparatus 20 on a first side 47*a*. A second load cell LC1 is positioned on the second side 47*b* also near the foot section 42. Third and fourth load cells LC2 and LC3 are positioned adjacent the head section 40 on the second side 47*b* and first side 47*a*, respectively. As noted above, the load cells 60 are positioned to sense the forces exerted by a load frame portion of the litter frame 26 onto an intermediate frame portion. Such forces may be exerted by the weight of a patient positioned on patient support deck 28, by objects placed on mattress 36, or by other people or objects. Accurate readings from the load cells 60 are important for various reasons, such as determining the weight fluctuations of a patient over time and the patient's center of gravity at any given time.

Figure 6:
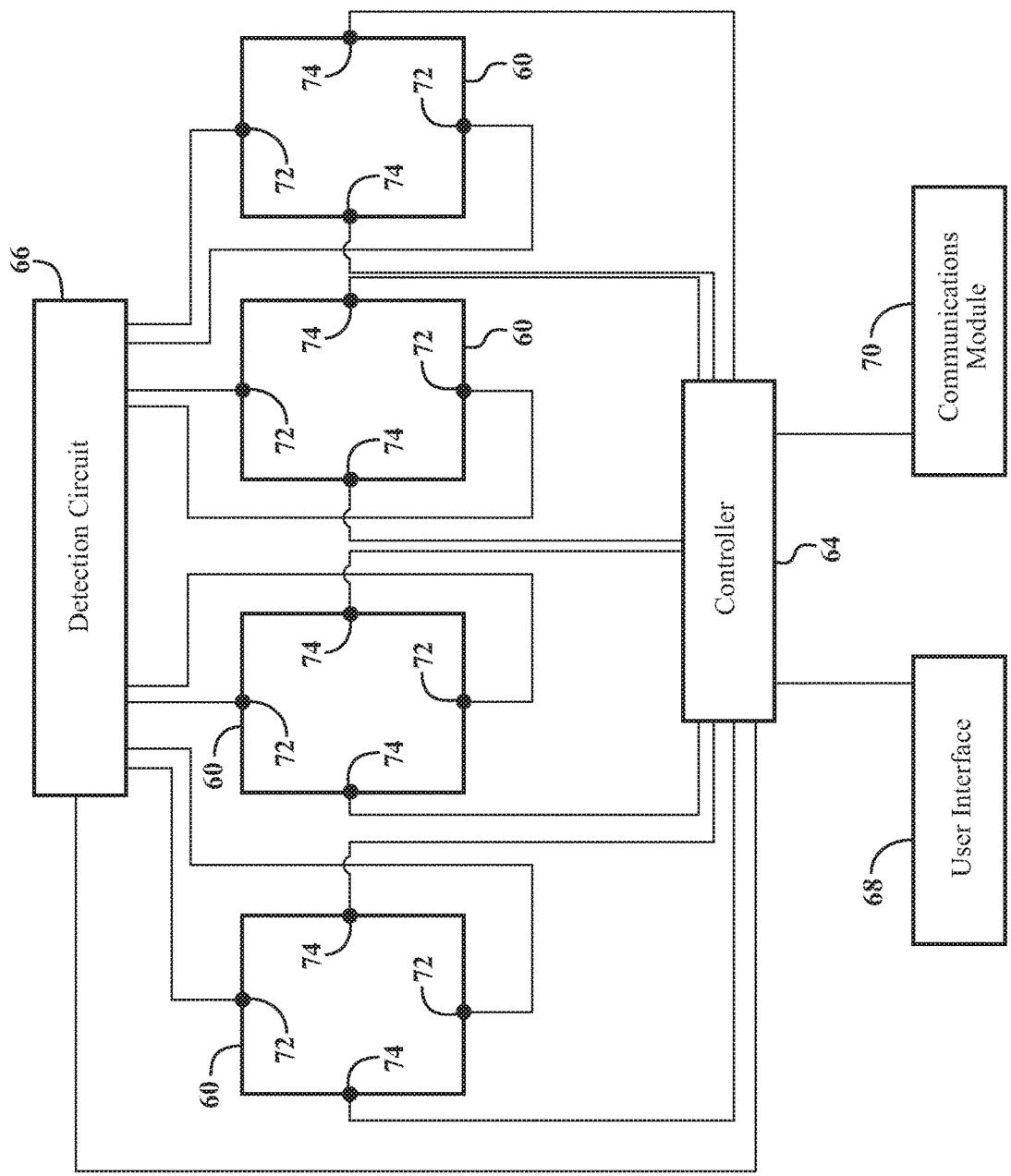
FIG. 6 is a schematic view of an exemplary load cell system that may be incorporated into a patient support apparatus.

FIG. 6 provides an exemplary block diagram of a load cell system 62 that may be useful with the present technology. The load cell system 62 may include the load cells 60, a controller 64, a detection circuit 66, a user interface 68, and a communication module 70. In various aspects, the load cell system 62 mainly functions as a scale system, although it may also be used as an exit detection system. When functioning as a scale system, the load cells 60 are configured to measure the amount of weight that is supported on the litter frame 26. Through the use of a tare control on the user interface 68, the weight of the litter frame 26 and other components of the patient support apparatus 20 can be separated from the weight reading such that a weight of just the patient/occupant can be determined. When the load cell system 62 functions as an exit detection system, the load cell system 62 is configured to determine when the patient/occupant has left or is likely to leave the apparatus. In various aspects, an alert or notification can be issued to appropriate personnel upon such detection, which is based on changes detected in the monitoring of the center of gravity of the patient.

The controller 64 may be in communication with detection circuit 66 and each load cell 60 as shown in FIGS. 5-6. The controller 64 is configured to read the outputs from each load cell 60 and determine, based on the combination of outputs, the total weight or load that is being supported on litter frame 26. In addition, the controller 64 may be configured to maintain and utilize a tare weight so that the weight of the patient 20 can be distinguished from the weight of the components of the patient support apparatus 20 and other non-patient items, such as bedding, pillows, etc. In various aspects, the controller 64 may be a microcontroller. In general, the controller 64 may include any one or more microprocessors, microcontrollers, field programmable gate arrays, systems on a chip, volatile or nonvolatile memory, discrete circuitry, and/or other hardware, software, or firmware that is capable of carrying out the instructions and functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by the controller 64 in carrying out the functions described herein, as well as the data necessary for carrying out these functions, may be stored in memory (not labeled) accessible to the controller 64. In addition to monitoring the outputs of the load cells 60, the load cell system controller 64 may also may control other aspects of the patient support apparatus 20 (e.g. motion), and/or may be in communication with one or more other controllers 54 that control the other aspects of the patient support apparatus 20.

The communications module 70 may include one or more transceivers that communicate with one or more off-board devices. In one aspect, the communications module 70 includes a Wi-Fi radio configured to communicate with wireless access points of a healthcare facility's computer network, thereby enabling the patient support apparatus 20 to communicate wirelessly with the computer network of the healthcare facility. The communications module 70 may also include an Ethernet connection, or other wired circuitry, for enabling wired communication with the hospital network, as well as nurse call cable circuitry for coupling to a nurse call cable that communicates with a nurse call system.

The optional detection circuit 66 may be configured to supply a substantially constant activation voltage to the load cells 60. The detection circuit 66 may also be configured to perform one or both of the following two additional functions: (1) detecting whether one or more of the load cells 60 are in an error state (e.g. they are not present, are not electrically coupled to the load cell system 62 properly, and/or are malfunctioning); and (2) detecting whether there are problems with the activation voltage supplied to the load cells 60. In carrying out either or both of these functions, the detection circuit 66 notifies controller 64 if it has detected an error with the load cells 60 and/or an error with respect to the activation voltage supplied to the load cells 60. The controller 64, in response, sends a message to the user interface 68 and/or communication module 70 indicating that an error has been detected. The user interface 68 and/or the remote device in communication with module 70 may then alert appropriate personnel in an audio, visual, and/or audiovisual manner. A similar circuit may be coupled to an accelerometer to detect error states and problems, and to notify appropriate personnel.

Each load cell 60 may include a pair of activation leads 72 and a pair of sensing or sensor leads 74 (FIG. 6). The detection circuit 66 is in electrical communication with the activation leads 72, but not with the sensor leads 74. The controller 64, in contrast, is in electrical communication with the sensor leads 74, but not the activation leads 72. One of each pair of the activation leads 72 of each load cell 60 is coupled to an activation voltage source, which supplies electrical power to the load cell 60, and the other of each pair of the activation leads 72 is coupled to ground. The sensor leads 74, rather than supplying electrical power, provide outputs to the controller 64 that are used to determine how much force is being exerted on load cells 60. That is, the sensor leads 74 provide outputs that are correlated to the forces sensed by load cells 60. In sum, the activation leads 72 provide power for the load cells 60 while the sensors leads 74 provide outputs that are indicative of the force applied against load cells 60.

Although not shown in FIG. 6, the load cells 60 may be configured as Wheatstone bridges, wherein one or more strain gauges that are internal to the load cell 60 are arranged in one or more legs of the Wheatstone bridge. The other legs consist of known resistances. In other words, one of the strain gauges is effectively responsible for one of the resistance values. (In some load cells, strain gauges are positioned in more than one leg of the Wheatstone bridge, but the strain gauges are geometrically arranged within the load cell to sense the same magnitude, but not necessarily direction, of the applied force). Typically, when no forces are detected by the strain gauges of the load cell 60, the current flowing through each of the two paths of the Wheatstone bridge is balanced, and there is substantially no voltage drop between the two midpoints. However, when a force is detected, the current is no longer balanced, and a voltage is detected between the two midpoints. The two midpoints correspond to the sensor leads 74 while the two activation leads 72 correspond to the endpoints of the Wheatstone bridge.

With renewed reference to FIG. 4, the load cells 60 may be removably coupled to the lift header assemblies 56, 58, for example, with suitable mechanical screws 76, washers, 78, and nuts 80. The load cells 60 may be provided with roller caps 82 to assist in smooth movement. Ground jumpers 84 can be provided coupling the load cells 60 to an appropriate ground connection. At least one cable (not shown) may be provided to couple the respective load cells 60 to the load cell system 62 and/or one or more controller 64, and may contain the various activation and sensor leads 72, 74.

As initially referred to above, one difficulty with accurately determining the patient's weight occurs when the patient support apparatus 20 is articulated (FIG. 1) or at positions other than the horizontally flat base position (FIG. 2) at which the load cells 60 are usually calibrated. For example, when the patient support surface 38 is angled with respect to the horizon or is otherwise articulated at various angles, the raw measurements on typical load cells will not reflect a patient's accurate weight because the center of gravity of the load shifts, thereby affecting the individual load signals sensed by each load cell 60. A measurement of the patient's weight independent of the bed's articulation is possible by calculating the bed's angle relative to baseline and load cell measurements.

One method to determine the angular position of a patient is by using gravitational accelerometers. When an accelerometer is in a stationary position, the only force acting on it is the vertical gravitational force having a constant acceleration. Accordingly, the angular position of the patient can be calculated by measuring the deviation in the inclination angle between the inclination axis and the vertical gravitational force. Although the accelerometers can provide an effective way to measure the inclination in the patient's position, the resolution of the gravitational accelerometers is restricted to a limited range of inclination angles. The resolution of the angular position of a patient can however be improved by using dual axis (X-Y) accelerometers to sense the inclination angle with a higher degree of accuracy over a broader range of inclination. Advantageously, the gravitational accelerometers can be orientated in a variety of mounted angles, independent of any reference to other components of the patient support apparatus 20. As a result, a particular accelerometer can be positioned such that its effective resolution specifically targets the anticipated range of inclination for a given application.

To provide a more complete assessment of a patient's position, a plurality of gravitational accelerometers 86 can be located in various parts of the patient support apparatus 20, for example connected to any parts of the patient support apparatus 20 that move. Output from the plurality of accelerometers 86 can be compiled to provide a three-dimensional view of the patient's position. The angular inclination readings from the X-axis channel or the Y-axis channel of an accelerometer can be independently selected. Moreover, the sensed inclinations can be used to complement measurements from other sensors in the patient support apparatus 20, such as load cells 60. In one aspect of the present technology, monolithic gravitational accelerometers may be employed to further reduce the inaccuracies associated with mechanical sensors.

In a patient support apparatus 20 according to one aspect of the present technology, measurements from the load cells 60 can be used together with the articulation angle of a section/region of the patient support surface 38 or the entire support deck 28 in order to determine, for example, a patient's weight. For example, when the patient support surface 38 is angled to the Trendelenburg and reverse Trendelenburg positions, the actual load can be calculated by knowing the angle of the region of the support deck 28 and respective loads measured by each load cell 60, independent of the support deck's position.

A tilt sensor 88 (FIG. 1), which incorporates an accelerometer 86, can also be used and may be attached to any part of the frame system of the patient support apparatus 20 that can be elevated, angled and/or articulated. The tilt sensor 88 can determine the angular position of the load frame while the center of gravity of the load shifts and provides a signal that is read and measurements are calculated after a given time period, such as 50 ms. It can run continuously, intermittently, or upon command from a user, such as when components of the patient support apparatus 20 are in an articulated position. The tilt sensor 88 may be connected to at least one computing system, processor, or any electronic board via a communications network, fiber optic, or wireless connection to allow for a reading of the tilt sensor signal.

Figure 7:
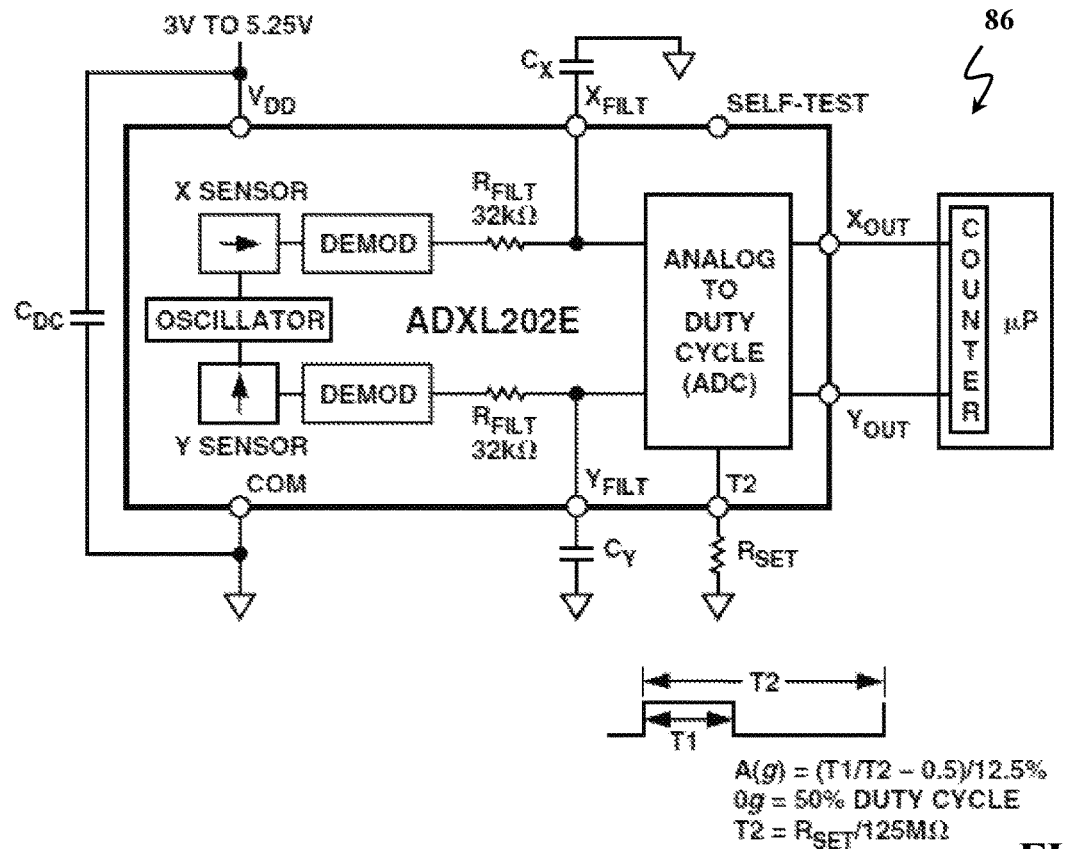
FIG. 7 provides an exemplary functional block diagram of an accelerometer useful with the present technology.

In one aspect, the tilt sensor 88 may be designed with a solid state accelerometer 86, such as the ADXL202E accelerometer from Analog Devices, Inc. of One Technology Way, Norwood, Mass., schematically represented in FIG. 7. Angular solid state sensors or electronic angular sensors, where a change in angle of the sensor changes the impedance of the sensor which can be measured, could also be used. Other accelerometers may also be used within the present technology. The accelerometer may be a 2-axis acceleration sensor with a direct interface to low-cost microcontrollers. One exemplary interface is possible through a duty cycle (ratio of the pulse width to the total period) output. For example, the outputs of the accelerometer can be analog or digital signals whose duty cycles are proportional to acceleration. The outputs can be directly measured with an integrated microprocessor counter, without any external converter.

As shown in FIG. 7, for each axis, a circuit output converts the signal into a modulated duty cycle that is decoded by the microprocessor. The accelerometer is typically capable of measuring positive and negative accelerations to at least +−2 g, so as to measure static acceleration forces such as gravity and therefore be used in a tilt sensor.

Theoretically, a 0 g acceleration produces a 50% nominal duty cycle. Acceleration is calculated as follows:

$$A(g)=(T_1/T_2-0.5)/12.5\%, \text{ with } T_2(s)=R_{SET}(\Omega)/125 \text{ M}\Omega$$

Figure 13:
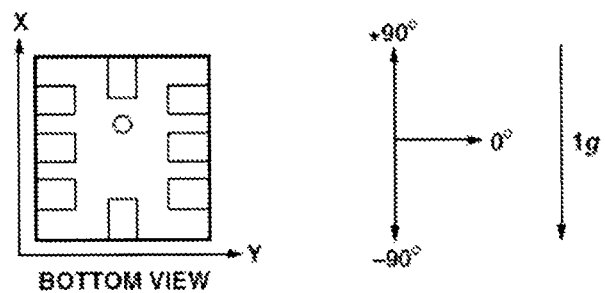
FIG. 13 provides an exemplary table that illustrates an output from an accelerometer that may vary based on tilt.

The 12.5% corresponds to the theoretical gain of the accelerometer. For example, when used as a tilt sensor, the accelerometer uses the force of gravity as the input vector to determine the orientation of the object in space. The accelerometer is more sensitive to tilt when the reading axis is perpendicular to the force of gravity, for example, parallel to the earth's surface. When the accelerometer is orientated on axis to gravity, for example, near its +1 g or −1 g reading, the change in output acceleration per degree of tilt is negligible. When the accelerometer is perpendicular, the output may vary nearly 17.5 mg per degree of tilt, but at 45 degrees the output only varies 12.2 mg by degree and the resolution declines. This is illustrated in the table provided in FIG. 13.

Notably, the gravity value varies according to the sine of the angle, which also influences the precision and consequently the orientation of the tilt sensor. The sensor precision can be improved by using both $X_{output}$ and $Y_{output}$ signals in the angular determination. By doing so, the low sensitivity range (around 0 degrees) is reduced.

Figure 8:
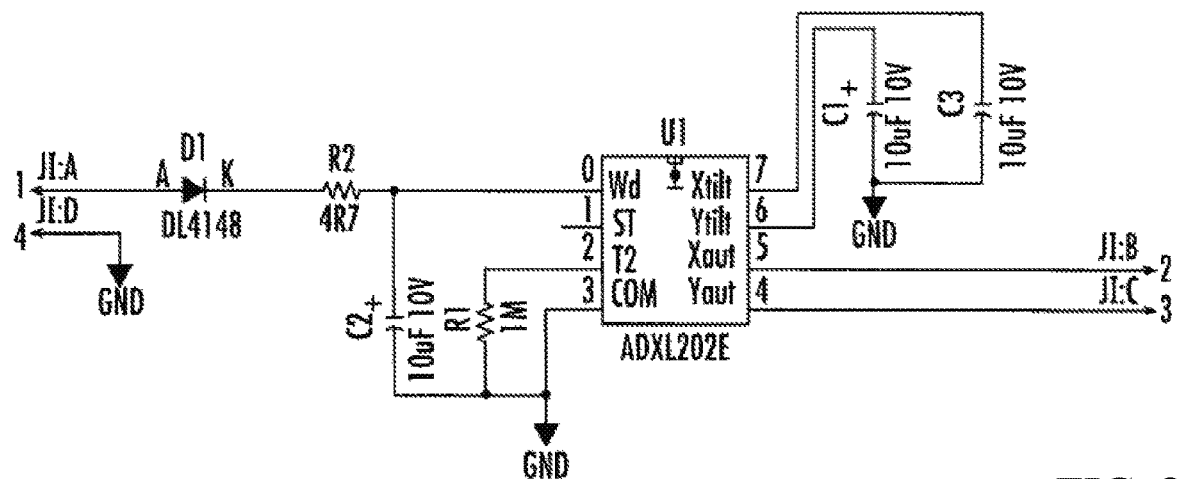
FIG. 8 provides an exemplary tilt sensor circuit according to one aspect.

The tilt sensor circuit used in one aspect was designed from the Analog Devices Inc. accelerometer following the recommended design parameters. The schematic of the circuit for this embodiment is shown in FIG. 8.

D1 is added to protect the circuitry against polarity inversion. $R_{SET}$ value was set to 1 MΩ. Therefore, $T_2$ value is:

$$T_2=1 \text{ M}\Omega/125 \text{ M}\Omega=0.008$$

$T_2$ total period is thus 8 ms, therefore giving a 125 Hz frequency.

In order to determine the actual values of the zero and the gain, the tilt sensor circuit must be calibrated. Since the zero and the gain are known after calibration, only $T_1/T_2$ is unknown. It is this duty cycle that varies according to the angle. The microprocessor thus takes this reading and calculates the corresponding angle.

The tilt sensor circuit includes an analog potentiometer that outputs a pulse width modulation (PWM) signal with a good signal-to-noise ratio. This PWM signal is sent to a microcontroller wherein the period of the signal is measured and the on-time of the signals. A ratio of these results is proportional to the sine of the angle. By using the cosine of this angle within a formula (discussed below) the precise angle can be determined. This analysis can be accomplished by a microprocessor.

To calibrate the tilt sensor circuit, two duty cycle readings must be taken at known angles. With these two PWM readings, the two unknowns (zero and gain) can be computed. It is preferable to take a PWM reading when the tilt sensor is at its zero position, as readings are usually precise at this position. This also provides a reading of the PWM value corresponding to the zero of the tilt sensor, since a sensor in zero position gives 0 g.

The tilt sensors of this embodiment are used to indicate the angle of the load frame, such as the Trendelenburg and reverse Trendelenburg angles. A compensation of the weight read by the load cells according to the Trendelenburg angle can then be computed. Consequently, the weight value displayed is thus in the required margin.

Figure 9:
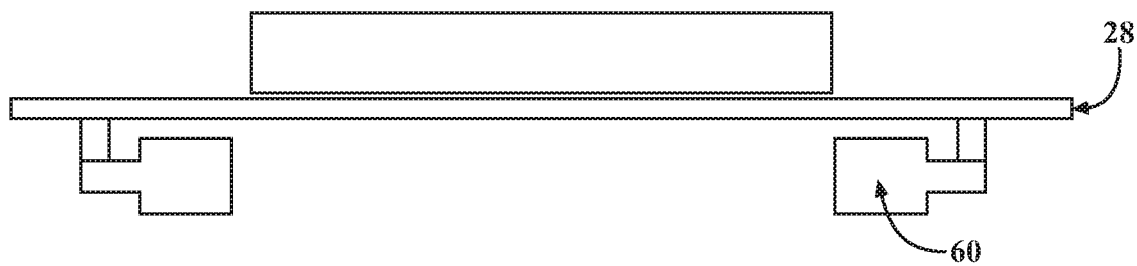
FIG. 9 depicts a horizontal patient support deck with a load according to one aspect.
Figure 10:
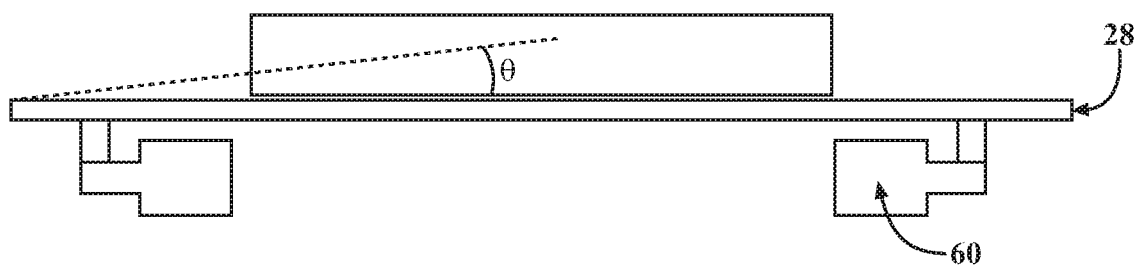
FIG. 10 depicts an inclined patient support deck with a load at angle $\Theta$ according to one aspect.

The axis in which the tilt sensor is positioned is important to obtain precise readings. For example, the position of a head section of the lying surface support may vary between 0 and 80 degrees. Given that the tilt sensor of the embodiment is more precise from −45 to 45 degrees than from 0 to 90 degrees, the tilt sensor would be positioned in the bed so that the zero of the sensor is at 45 degrees. In computation, one would account for this position by adding 45 degrees to each angle read. The calculation of load and calibration values is apparent in referring to FIGS. 9 and 10, where:

X is a patient load;
$Y_+$ is a weight of a patient support frame that changes with the Trendelenburg angle;
$Z_+$ is a load cell factor not influenced by the Trendelenburg angle;
$Y_-$ is a weight of bed frame which changes with the reverse Trendelenburg angle;

$Z_-$ is a load cell factor not influenced by the reverse Trendelenburg angle;

$\Theta$ is a bed frame angle; and

T's are load cell readings.

At $\Theta=0°$, $T_0°=X+Y_++Z_+$

At $\Theta=12°$, $T_{12}°=(X_++Y_+)\cos\Theta+Z_+$

During calibration, the load frame without the patient is measured at 0° and at 12°, providing:

$$X = 0$$

$$T_0° = \text{first measurement at } 0°$$

$$T_{12}° = \text{second measurement at } 12°$$

$$T_0° = Y_+ + Z_+$$

$$T_{12}° = Y_+\cos\theta + Z_+$$

$$Y_+ = T_0° - Z_+$$

$$Y_+\cos\theta = T_{12}° - Z_+$$

$$Y_+ = \frac{T_{12}° - Z_+}{\cos\theta}$$

$$T_0° - Z_+ = \frac{T_{12}° - Z_+}{\cos\theta}$$

$$Z_+ = \frac{T_{12}° - T_0°\cos\theta}{1 - \cos\theta}$$

If $\theta = 12$, $Z_+ = \frac{T_{12}° - T_0°\cos 12°}{1 - \cos 12°}$ $$Z_+ = (T_{12}° - T_0° * 0.97815) * 45.761565$$

$$Y_+ = T_0° - Z_+$$

$Z_+$ and $Y_+$ for each load cell are determined during calibration. In a similar manner, $Z_-$ and $Y_-$ are determined using measurements at 0° and −12°, providing:

$$Z_- = (T_{-12}° - T_0° * 0.97815) * 45.761565$$

$$Y_- = T_0° - Z_-$$

When determining the patient's weight, X, the following calculations are made for each load cell:

$$T_\theta = (X + Y)\cos\theta + Z$$

$$T_\theta = X\cos\theta + Y\cos\theta + Z$$

$$X\cos\theta = T_\theta - Y\cos\theta - Z$$

$$X = \frac{T_\theta - Y\cos\theta - Z}{\cos\theta}$$

$$X = \frac{T_\theta - Z}{\cos\theta} - Y$$

The processor determines the load frame's angular position (Trendelenburg or reverse Trendelenburg) prior to choosing $Y_+$ or $Y_-$ and $Z_+$ or $Z_-$. When the load frame's angle is 0°, the processor chooses $Y_+$ and $Z_+$ to calculate the load.

The center of gravity can be calculated as follows, using for example four load cells positioned in a rectangle relative to the patient:

X is a length (head to foot)

Y is a width (left to right)

LC(0) is a load cell value foot left

LC(1) is a load cell value foot right

LC(2) is a load cell value head right

LC(3) is a load cell value head left

W is a total weight of the patient

H(X) is a distance between the head load cells and foot load cells

H(Y) is a distance between the right load cells and left load cells $$CG[X] = \frac{LC(3) + LC(1)}{\frac{W}{100}} * H(X) * 0.01$$

$$CG[Y] = \frac{LC(3) + LC(0)}{\frac{W}{100}} * H(Y) * 0.01$$

Figure 11:
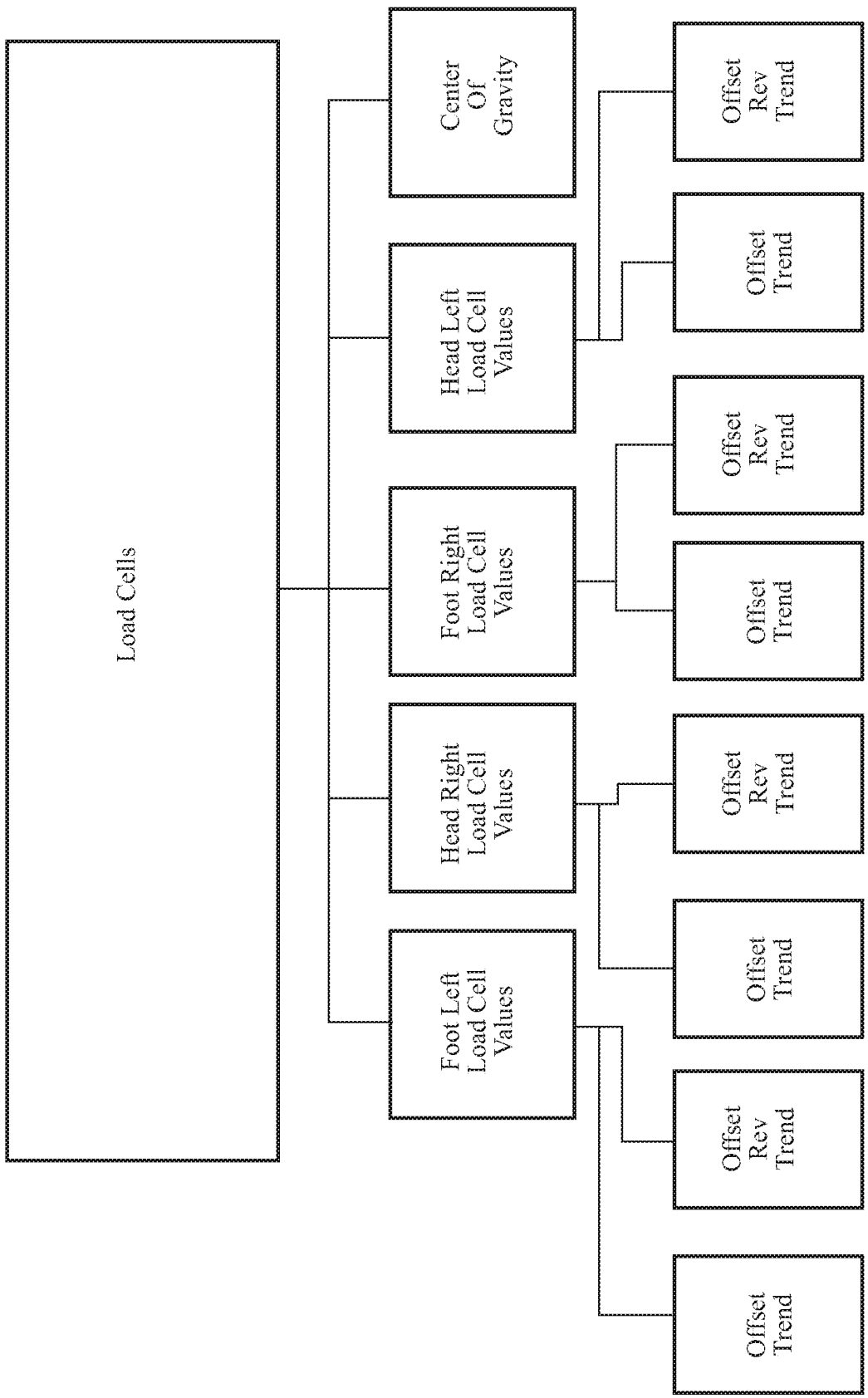
FIG. 11 provides another aspect of a load cell system that can be used for monitoring movement, or evaluating a mass/weight of a supported patient.

The configuration of a load cell system as shown in FIG. 11 may be useful for monitoring movement of a patient. The system can be integrated into the bed or can be part of a patient support surface, such as a mattress. In addition, the load cell system can include a number of load cells or load sensors, for example a load cell that can be embedded in the patient support apparatus proximally positioned at each of a supported person's limbs and optionally at the center of the patient support apparatus. The load cell system also can include a mesh of load cells in one example. The signals from the load cells can be monitored and processed by a processing unit in the load cell system or a central processing unit capable of monitoring, processing, and controlling signals from the patient support apparatuses various subsystems. Instead of forming a part of a patient support surface, such as a mattress, the load cell system can also be integrated into the patient support surface. The load cell system can provide a measure for the pressure, weight, or mass load of a certain load cell, for example foot left or right load cell values and head left or right load cell values and additional information about the location of the center of gravity.

In one aspect of the present technology, the tilt sensors 88 can provide a means for determining possible interference between components of the bed. For example, if a particular component is in a certain relative position, a second component might not be able to perform certain functions associated with it. In this aspect, there can furthermore be a movement termination based on the evaluation of tilt sensors readings.

In a further aspect, tilt sensors 88 can be used to evaluate a patient's position over a period of time through the collection of angle variation data. A collection of angular data from the tilt sensors can also provide assistance for the maintenance of the patient support apparatus 20. For example it can help to determine the angle of a particular component and the period of time that that position is held, especially when a particular position results in higher stress levels being applied to specific components of the bed.

In another aspect, tilt sensors 88 can be positioned on an elevation component for a determination of the height of the bed surface. The tilt sensors 88 may use wireless communication. If the tilt sensors do not have an on-board power supply they can be powered in the same way as an RFID tag, by the scanning frequencies sent by a scanner for example. In another aspect, the tilt sensors may be integrated within the load cells 60. As can be appreciated, the tilt sensors 88 can be positioned with a plurality of other components of the patient support apparatus 20, for example, in the side rails, a control panel, on an intravenous apparatus support (not shown) that may be attached to a patient support apparatus 20, etc.

In one aspect, the control and diagnostic system can include an additional scale subsystem providing a calibration process for calibrating the scale subsystem to provide accurate reading of a patient's weight and subsequently to calibrate a motion detection system for monitoring movement of the patient. It may be necessary to calibrate the load cells' electronics in order to provide match the sensor signals with the scale subsystem electronics. The tilt sensors 88 can also be used with a control and diagnostic system as a means for fault detection. For example, where no change in an angle is detected when an actuator is being activated to modify the angle, the situation can be indicative of a blockage related to the actuator movement or an actuator malfunction.

The teachings of the present technology additionally include the calibration of the accelerometer 86 using at least one of the load cells 60. In various aspects, the accelerometer 86 may be part of a tilt sensor 88, as described in detail above. In still other aspects, the methods disclosed herein include independently calibrating first and second accelerometers (or more), for example, coupled to components at opposing ends of the patient support apparatus.

Figure 12:
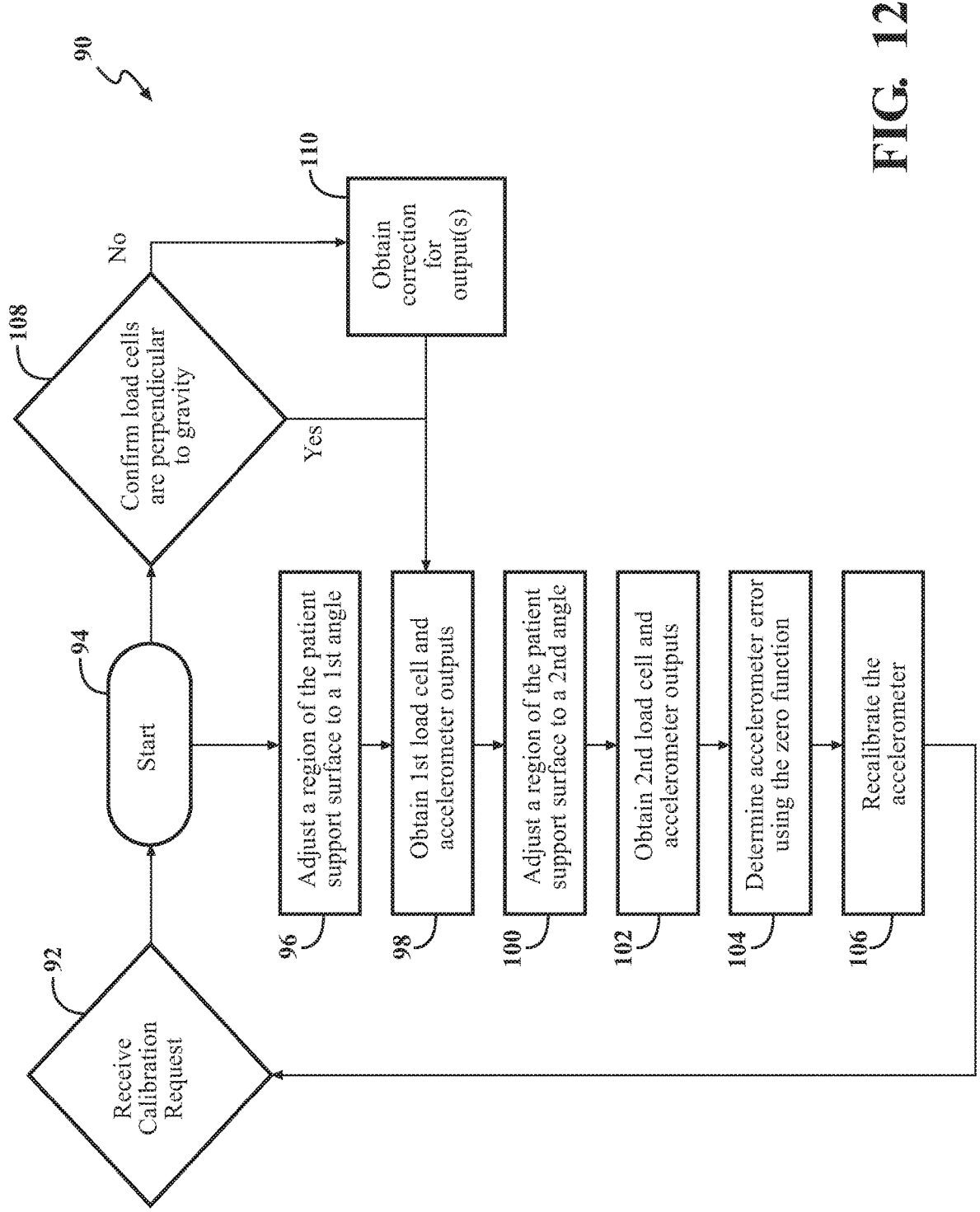
FIG. 12 provides an exemplary flowchart that illustrates the basic framework for the automated systems and methods for calibrating an accelerometer according to various aspects of the present technology.

FIG. 12 provides an exemplary flowchart 90 that illustrates the basic framework for the automated systems and methods for calibrating an accelerometer 86 according to various aspects of the present technology. While the flowchart 90 provides a certain path of steps and features, as well as an order that may be followed for illustration purposes, it should be understood that the methods of the present technology should not be interpreted as having a fixed order of steps, features, or procedures, and various steps, features, and procedures can be performed in different orders of operation, at different stages, and by different patient support apparatuses. Further, certain features may be performed repeatedly or monitored continuously. Various functions, methods, features, and steps are disclosed in terms of block diagrams with decision trees. However, it should be understood that certain of these functions may be enacted or performed in dedicated hardware circuitry or programmed software routines as a computer readable storage medium capable of execution as instructions in a microprocessor-based electronics control embodiment, such as a control system or controller, as will be discussed below. Memory is one example of a non-transitory computer-readable medium/storage media having embodied thereon computer-useable instructions that, when executed, may coordinate and/or perform one or more method feature according to the present technology.

In various aspects, the methods may begin by receiving a request for calibration as indicated by method feature 92. An exemplary request may be encoded in an electrical signal. In certain aspects, a care giver or technician may operate a user interface coupled to a controller and/or one or more processors in order to begin the calibration process. In still other aspects, the controller and/or the one or more processors may be configured to initiate a calibration process after a predetermined period of time has passed since the last calibration, or when they detect any environmental changes that are indicative of a need for calibration. As shown by method feature 94, once the request for calibration is received (or the controller is otherwise directed), the systems and methods are configured to start the calibration process to obtain various data and outputs that will be used in the calibration algorithms. The methods disclosed herein rely on at least two sets of output data obtained at two different trend angles from a load cell and the accelerometer to be calibrated. Preferably the roll-off of the angles is identical in the two ± directions. For example, one set of data is obtained at a trend angle of −15 degrees, and the other set of data is obtained at +15 degrees; or one set of data is obtained at a trend angle of −20 degrees, and the other set of data is obtained at +20 degrees. As indicated by method feature 96, the methods may include adjusting a region of the patient support surface to the first trend angle, and as indicated by method feature 98, obtaining load data from a load cell including a first load output ($L_1$) detected at the region of the patient support surface when disposed at a first trend angle with respect to a horizontal plane. The method also provides for obtaining angle data from an accelerometer including a first angle output ($\Theta_1$) representative of the first trend angle.

As indicated by method feature 100, the methods continue by adjusting the same region of the patient support surface to the second trend angle, and as indicated by method feature 102, obtaining load data from a load cell including a second load output ($L_2$) detected at the region of the patient support surface when disposed at a second trend angle with respect to the horizontal plane. The method also provides for obtaining angle data from an accelerometer including a second angle output ($\Theta_2$) representative of the second trend angle.

As indicated by method feature 104, and discussed in more detail below, once all of the calibration data is obtained, the methods may include determining an error (A) in the accelerometer reading by using a zero function, and recalibrating the accelerometer as indicated by method feature 106.

In various aspects, depending on the particular type of patient support apparatus, there may be instances when the load cells are provided at an angle. For example, the load cells may be coupled to a tilting component that is not substantially perpendicular to a direction of gravity. In other instances, a portion of a litter frame or other component coupled to the load cell may bend over time. Accordingly, as shown by method feature 108, prior to calibrating the accelerometer, the methods of the present technology may include using a controller is configured to confirm the load cell is substantially perpendicular to a direction of gravity prior to obtaining the output data. In this regard, and as shown by method feature 110, if it is determined that the load cell is not substantially perpendicular to a direction of gravity, the methods may include using the controller and/or one or more processors to correct at least one output data prior to using the data for calibrating the accelerometer.

The load cell readings are governed by the relationship of:

$$L = W \cdot \cos(T), \text{ where:}$$

L is the load cell reading;

W is a total weight of the patient; and

T is the apparent trend angle, which is the sum of the current accelerometer reading ($\Theta$)+any error (A), for example, $T=(\Theta+A)$, In order to calibrate the accelerometer, the present technology obtains first and second readings of a load cell taken at opposing angles of inclination (±T). In various aspects, it is preferred that the angles of inclination are in a range of from about ±10 and about ±35 degrees, and more preferably in a range of from about ±15 to about ±30 degrees. With first and second load cell readings ($L_1$ and $L_2$), the relationship is provided as follows:

$$L_1 = W \cdot \cos(\Theta_1 + A)$$

$$L_2 = W \cdot \cos(\Theta_2 + A)$$

Since the load cell output readings $L_1$ and $L_2$ should be the same at both opposing angles of inclination, the equations can be rearranged as follows:

$$L_2 \cdot \cos(\Theta_1 + A) = L_1 \cdot \cos(\Theta_2 + A)$$

where the zero function for A can be calculated in order to obtain the accelerometer error that can be used for the recalibration purposes.

In one specific example, the following conditions are used to calculate the accelerometer error:
Litter is 200 lb
Weight of the patient is 100 lb
A is 1°
$\Theta_1 = -15°$ $T_1 = (\Theta_1 + A) = -14°$
$\Theta_2 = 15°$ $T_2 = (\Theta_2 + A) = 16°$
$L_1 = W \cdot \cos(\Theta_1 + A) = 100 \cdot \cos(-14°) = 97.03$
$L_2 = W \cdot \cos(\Theta_2 + A) = 100 \cdot \cos(16°) = 96.13$
Solving for the zero function of A using the equation:

$$L_2 \cdot \cos(\Theta_1 + A) = L_1 \cdot \cos(\Theta_2 + A)$$

$97.03 \cdot \cos(-15 + A) = 96.13 \cdot \cos(15 + A)$
leads to $A = -1°$
Referring back to $L_1 = W \cdot \cos(\Theta_1 + A)$:
The display weight, $W = L_1 / \cos(\Theta_1 + A)$, which provides: $W = 97.03 / \cos(-15) = 100.45$, which is an error of 0.45 lbs/100 lbs Assuming that an appropriate litter frame weighs 200 lbs, the total weight of the patient and the litter frame is 300 lbs, which leads to an overall display of 301.35 (having an error of 1.35 lbs). Once the algorithm tares out the 200 lb litter frame, the weight of the patient becomes 101.35 lbs, which is an error of 1.35%. This error is then used to recalibrate the accelerometer.

The foregoing description is provided for purposes of illustration and description and is in no way intended to limit the disclosure, its application, or uses. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations should not be regarded as a departure from the disclosure, and all such modifications are intended to be included within the scope of the disclosure.

As used herein, the phrase at least one of A, B, and C should be construed to mean a logical (A or B or C), using a non-exclusive logical "or." It should be understood that the various steps within a method may be executed in different order without altering the principles of the present disclosure. Disclosure of ranges includes disclosure of all ranges and subdivided ranges within the entire range, including the endpoints.

As used herein, the terms "comprise" and "include" and their variants are intended to be non-limiting, such that recitation of items in succession or a list is not to the exclusion of other like items that may also be useful in the devices and methods of this technology. Similarly, the terms "can" and "may" and their variants are intended to be non-limiting, such that recitation that an embodiment can or may comprise certain elements or features does not exclude other embodiments of the present technology that do not contain those elements or features.

The broad teachings of the present disclosure can be implemented in a variety of forms. Therefore, while this disclosure includes particular examples, the true scope of the disclosure should not be so limited since other modifications will become apparent to the skilled practitioner upon a study of the specification and the following claims. Reference herein to one aspect, or various aspects means that a particular feature, structure, or characteristic described in connection with an embodiment or particular system is included in at least one embodiment or aspect. The appearances of the phrase "in one aspect" (or variations thereof) are not necessarily referring to the same aspect or embodiment. It should be also understood that the various method steps discussed herein do not have to be carried out in the same order as depicted, and not each method step is required in each aspect or embodiment.

What is claimed is:

1. A patient support apparatus comprising:
   a litter frame;
   a deck supported by the litter frame and movable relative to the litter frame between a horizontal position and various angled positions;
   a patient support surface arranged on the deck and configured to support a patient thereon, the patient support surface having at least one region configured to be disposed at an angular position;
   a load cell supporting the region and configured to generate load data including:
      a first load output ($L_1$) detected at the region of the patient support surface when disposed at a first trend angle with respect to a horizontal plane; and
      a second load output ($L_2$) detected at the region of the patient support surface when disposed at a second trend angle with respect to the horizontal plane,
   an accelerometer configured to generate angle data including:
      a first angle output ($\Theta_1$) representative of the first trend angle; and
      a second angle output ($\Theta_2$) representative of the second trend angle;
   one or more processors; and
   a controller in communication with the load cell and the accelerometer, the controller including instructions that when executed by the one or more processors cause the one or more processors to, in response to acquiring the load data and the angle data, determine an error in the angle data and calibrate the accelerometer.

2. The patient support apparatus according to claim 1, wherein the controller is configured to calibrate the accelerometer based on a calculation of a zero function for an accelerometer error (A) using the following equation:

$$L_2 \cdot \cos(\Theta_1 + A) = L_1 \cdot \cos(\Theta_2 + A).$$

3. The patient support apparatus according to claim 2, wherein the first and second trend angles are within a threshold range of from about ±15 to about ±30 degrees.

4. The patient support apparatus according to claim 1, wherein the controller comprises a memory configured to retain calibration data.

5. The patient support apparatus according to claim 4, further comprising a user interface configured to provide retained calibration data to a user.

6. The patient support apparatus according to claim 1, wherein the accelerometer is a component of a tilt sensor coupled to the deck.

7. The patient support apparatus according to claim 1, comprising a pair of accelerometers, each accelerometer being mounted to an opposing end of the deck and being independently calibrated.

8. The patient support apparatus according to claim 1, wherein the controller is configured to output an error signal if the load cell or the accelerometer is in an error state.

9. The patient support apparatus according to claim 1, wherein the controller is configured to recalibrate the accelerometer after a predetermined period of time.

10. The patient support apparatus according to claim 1, wherein the controller is configured to confirm the load cell is substantially perpendicular to a direction of gravity prior to calibrating the accelerometer.

11. The patient support apparatus according to claim 1, wherein the controller is configured to determine that the load cell is not substantially perpendicular to a direction of gravity; and the controller corrects at least one output prior to calibrating the accelerometer.

12. A method for calibrating an accelerometer of a patient support apparatus, the method comprising:
receiving a request for calibration of an accelerometer;
obtaining load data from a load cell supporting a region of a patient support surface, the load data including: a first load output ($L_1$) detected at the region of the patient support surface when disposed at a first trend angle with respect to a horizontal plane, and a second load output ($L_2$) detected at the region of the patient support surface when disposed at a second trend angle with respect to the horizontal plane;
obtaining angle data from an accelerometer coupled to a movable deck of the patient support apparatus, the angle data including: a first angle output ($\Theta_1$) representative of the first trend angle; and a second angle output ($\Theta_2$) representative of the second trend angle; and
calibrating the accelerometer, using a controller in communication with the load cell and the accelerometer, based on the respective load data and angle data.

13. The method according to claim 12, wherein the controller is configured to calibrate the accelerometer based on a calculation of a zero function for an accelerometer error (A) using the following equation:

$$L_2 \cdot \cos(\Theta_1 + A) = L_1 \cdot \cos(\Theta_2 + A).$$

14. The method according to claim 13, wherein the first and second trend angles are within a threshold range of from about ±15 to about ±30 degrees.

15. The method according to claim 12, further comprising storing calibration data in a memory of the controller.

16. The method according to claim 12, further comprising confirming the load cell is substantially perpendicular to a direction of gravity prior to calibrating the accelerometer.

17. The method according to claim 12, further comprising:
determining that the load cell is not substantially perpendicular to a direction of gravity; and
correcting at least one output prior to calibrating the accelerometer.

18. The method according to claim 12, wherein the accelerometer is a component of a tilt sensor coupled to the movable deck.

19. The method according to claim 12, comprising independently calibrating first and second accelerometers coupled to opposing ends of the patient support apparatus.

20. The method according to claim 12, wherein the controller is configured to output an error signal if the load cell or the accelerometer is in an error state.

* * * * *

UNITED STATES PATENT AND TRADEMARK OFFICE
CERTIFICATE OF CORRECTION

PATENT NO.         : 10,940,065 B2
APPLICATION NO.    : 16/549612
DATED              : March 9, 2021
INVENTOR(S)        : William Childs, Gary Bartley and Connor St. John It is certified that error appears in the above-identified patent and that said Letters Patent is hereby corrected as shown below:

In the Specification

Column 11, Line 13: delete "$T_0^\circ$ = first measurement at 0°" and insert -- $T_0° = $ *first measurement at 0°* --

Column 11, Line 14: delete "$T_{12}^\circ$ = second measurement at 12°" and insert -- $T_{12}° = $ *second measurement at 12°* --

Column 11, Line 15: delete "$T_0^\circ = Y_+ + Z_+$" and insert -- $T_0° = Y_+ + Z_+$ --

Column 11, Line 16: delete "$T_{12}^\circ = Y_+ \cos\theta + Z_+$" and insert -- $T_{12}° = Y_+ \cos\theta + Z_+$ --

Column 11, Line 19: delete "$Y_+ = T_0^\circ - Z_+$" and insert -- $Y_+ = T_0° - Z_+$ --

Column 11, Line 20: delete "$Y_+ \cos\theta = T_{12}^\circ - Z_+$" and insert -- $Y_+ \cos\theta = T_{12}° - Z_+$ --

Column 11, Line 22: delete "$Y_+ = \frac{T_{12}^\circ - Z_+}{\cos\theta}$" and insert -- $Y_+ = \frac{T_{12}° - Z_+}{\cos\theta}$ --

Column 11, Line 24: delete "$T_0^\circ - Z_+ = \frac{T_{12}^\circ - Z_+}{\cos\theta}$" and insert -- $T_0° - Z_+ = \frac{T_{12}° - Z_+}{\cos\theta}$ --

Column 11, Line 26: delete "$Z_+ = \frac{T_{12}^\circ - T_0^\circ \cos\theta}{1 - \cos\theta}$" and insert -- $Z_+ = \frac{T_{12}° - T_0° \cos\theta}{1 - \cos\theta}$ --

Column 11, Line 28: delete "If $\theta = 12$, $Z_+ = \frac{T_{12}^\circ - T_0^\circ \cos 12°}{1 - \cos 12°}$" and insert -- *If* $\theta = 12$, $Z_+ = \frac{T_{12}° - T_0° \cos 12°}{1 - \cos 12°}$ --

Signed and Sealed this
Twenty-eighth Day of December, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,940,065 B2

Column 11, Line 29: delete "$Z_+ = (T_{12}^\circ - T_0^\circ * 0.97815) * 45.761565$" and insert -- $Z_+ = (T_{12}^\circ - T_0^\circ * 0.97815) * 45.761565$ --

Column 11, Line 31: delete "$Y_+ = T_0^\circ - Z_+$" and insert -- $Y_+ = T_0^\circ - Z_+$ --

Column 11, Line 40: delete "$Y_- = T_0^\circ - Z_-$" and insert -- $Y_- = T_0^\circ - Z_-$ --

Column 15, Line 16: delete "L₁=W·cos(Θ₁+A)=100·cos)(–14°)=97.03" and insert -- $L_1 = W \cdot \cos(\Theta_1 + A) = 100 \cdot \cos(-14°) = 97.03$ --

Column 15, Line 17: delete "$L_2 = W \cdot \cos(\Theta_2 + A) = 100 \cdot \cos)(16°) = 96.13$," and insert -- $L_2 = W \cdot \cos(\Theta_2 + A) = 100 \cdot \cos(16°) = 96.13$ --